United States Patent [19]

Riva et al.

[11] Patent Number: 4,908,351

[45] Date of Patent: Mar. 13, 1990

[54] ANTIBIOTIC A 42867 DERIVATIVE

[75] Inventors: Ernesto Riva; Maurizio Denaro, both of Milano; Pietro Ferrari, Ferriere; Giovanni Cassani, Pavia, all of Italy

[73] Assignee: Merrell Dow Pharmaceuticals Inc., Cincinnati, Ohio

[21] Appl. No.: 304,421

[22] Filed: Jan. 24, 1989

[30] Foreign Application Priority Data

Jan. 28, 1988 [GB] United Kingdom ............... 8801899

[51] Int. Cl.$^4$ ..................... A61K 37/02; C07K 5/12
[52] U.S. Cl. ......................................... 514/8; 435/169; 530/317; 530/322
[58] Field of Search ................. 514/8; 530/322, 317, 530/319, 320; 435/169

[56] References Cited

U.S. PATENT DOCUMENTS 3,067,099 12/1962 McCormick et al. ............. 424/115
3,700,768 10/1972 Kunstmann et al. ............. 435/169
4,804,534 2/1989 Riva et al. ......................... 435/169

FOREIGN PATENT DOCUMENTS 0213111 8/1987 European Pat. Off. ............. 514/8

Primary Examiner—Lester L. Lee
Attorney, Agent, or Firm—J. Michael Dixon

[57] ABSTRACT

The present invention is directed to a new antibiotic substance denominated antibiotic A 42867 pseudoaglycon, a pharmaceutically acceptable salt thereof, a process for its preparation from antibiotic A 42867 and pharmaceutical compositions containing the new substance of the invention.

11 Claims, 4 Drawing Sheets

ANTIBIOTIC A 42867 DERIVATIVE

The present invention is directed to a new antibiotic substance denominated antibiotic A 42867 pseudoaglycon, a pharmaceutically acceptable salt thereof, a process for its preparation from antibiotic A 42867 and pharmaceutical compositions containing the new substance of the invention.

Antibiotic A 42867 pseudoaglycon and the pharmaceutically acceptable salts thereof are particularly active against gram positive bacteria.

Antibiotic A 42867, which is the starting material for the preparation of the compound of the invention, is an antibiotic substance produced by a Nocardia strain, Nocardia sp. ATCC 53492, which was deposited on 23 May 1986 under the provisions of the Budapest Treaty. It was described in European Patent Application Publication No. 254999.

On the basis of the physico-chemical data available and by reference to the structure of known substances the following formula can be attributed to antibiotic A 42867

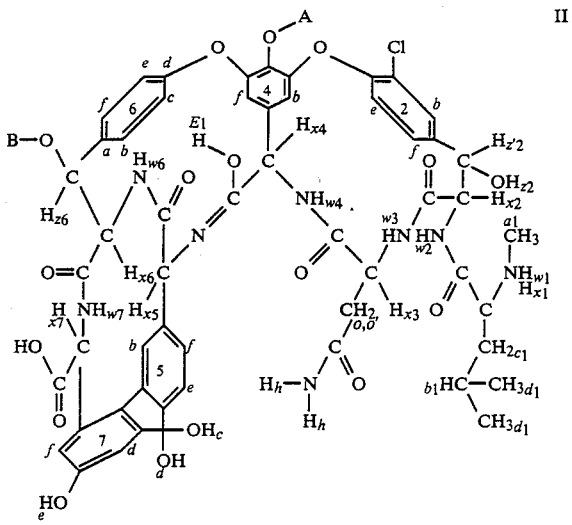

II wherein

A represents a disaccharide residue of one unit of glucose and one unit of d-rhamnose, of formula, respectively:

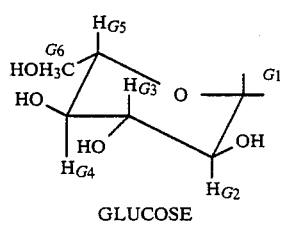

GLUCOSE

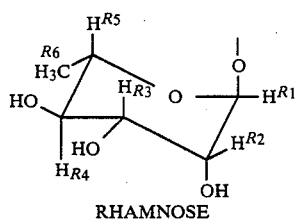

RHAMNOSE

-continued
(α anomer)

and

B represents a beta-vancosamine unit of formula

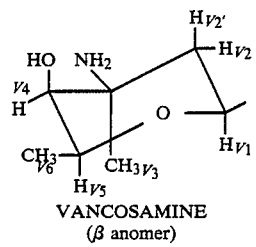

VANCOSAMINE
(β anomer)

As evident to the man skilled in the art, the peptidic bond connecting the moiety containing ring 4 with that containing ring 5 may exist in a tautomeric form (—CO—NH—). In the present disclosure, the above formula I is thus intended to cover also its tautomers.

Physico-chemical characteristics of antibiotic A 42867 pseudoaglycon:

A) ultraviolet absorption which is reported is FIG. 1 and exhibits the following absorption maxima:

|     |                      | Lambda max (nm) |
| --- | -------------------- | --------------- |
| (a) | 0.1 N HCl            | 279             |
| (b) | Water                | 279             |
|     |                      | 305 (shoulder)  |
| (c) | phosphate buffer pH 7.4 | 279          |
| (e) | 0.1 N KOH            | 299             |
|     |                      | 265 (shoulder)  |

(B) infrared absorption spectrum in nujol mull which is shown in FIG. 2 of the accompanying drawings and exhibits the following absorption maxima (cm$^{-1}$): 3700–3100, 3000–2800 (nujol); 1650; 1590; 1460 (nujol); 1375 (nujol); 1305; 1240; 1210; 1160; 1130; 1060; 1010; 950; 870; 835; 720 (nujol)

(C) $^1$H-NMR spectrum which is shown in FIG. 3 and exhibits the following groups of signals (in ppm) at 250 MHz (Bruker Instruments) recorded in DMSO d$_6$ (hexadeuterodimethylsulfoxide) using TMS as the internal standard (0.00 ppm), (delta=ppm):

Sugar moiety:

1.22, d [CH$_3$—(CH)]; 1.50,s [CH$_3$—C(NH$_2$)]; 2.25, m [CH$_2$—(CH)]; 3.60, m [CH—(CH$_3$)]; 4.90, d (anomeric proton)

Core moiety:

1.74, m [CH(CH$_3$)$_2$];

1.60, m [CH$_2$(⟨CH / CH⟩)];

2.32, s [CH$_3$—(NH)]; 2.49,s (solvent DMSOd$_5$); 3.35, br [H$_2$O]; 4.23–6.35 [aromatic and peptidic CH's]; 6.35–9.50 [aromatic CH's, peptidic NH's and phenolic OH's]

s=singlet; d=doublet; m=multiplet; br=broad (D) retention time ($R_t$) of 2.88 relative to antibiotic A 42867 ($R_t$=8.45 min) when analyzed by reverse phase HPLC under the following conditions:

column: Ultrasphere ODS (5 micrometer) Altex (Beckman) 4.6 mm (i.d.)×250 mm pre-column: 3 cm Brownlee Labs RP 18 (5 micrometer)

eluents:

(A) (2.5 gr/l) $NaH_2PO_4/CH_3CN$, 98:2 (v/v) adjusted to pH 6.0

(B) (2.5 gr/l) $NaH_2PO_4/CH_3CN$, 30:70 (v/v) adjusted to pH 6.0

Elution mode: linear gradient from 5% to 60% of B in A in 40 min flow rate: 1.8 ml/min U.V. detector: 254 nm internal standard: antibiotic A 42867 ($R_t$=8.45 min)

(E) elemental analysis showing the presence of one chlorine atom per molecule (F) 2D$^1$H-NMR NOESYPH analysis showing that the molecular chlorine atom is on ring 2 and not on ring 6, on the basis of Nuclear Overhauser effect (dipolar coupling through space) and scalar coupling through chemical bond, in fact:

(a) on the basis of scalar coupling, proton 2b (see formula I) shows only a meta coupling with 2f but no ortho coupling; (proton 2b is on ring 2 and not on ring 6 on the basis of the following dipolar coupling: 2b→Z′2; 2b→(Z2)OH; (Z2)OH→Z′2; Z′2→X2)

(b) on the basis of scalar coupling, proton 6b (see formula I) shows an ortho coupling with proton 6c (dipolar coupling 6b→6c; Z6-6b; Z6→X6)

(G) a fast atom bombardament (FAB) mass spectrum with M+N$^{30}$ at about 1251 (the theoretical cluster ion peaks for the formula $C_{60}H_{64}N_9O_{19}Cl+H$ range from 1250 to 1255, average value 1251.68). The FAB spectrum was obtained with a VG 70-250 instrument, bombarding gas Xenon; beam energy 8 KeV; accelerating voltage 6 kV; matrix thioglycerol-glycerol, 2:1.

(H) acid and basic functions capable of forming salts.

On the basis of the above data and by reference to the structure of known antibiotics, it can tentatively be attributed to the following formula:

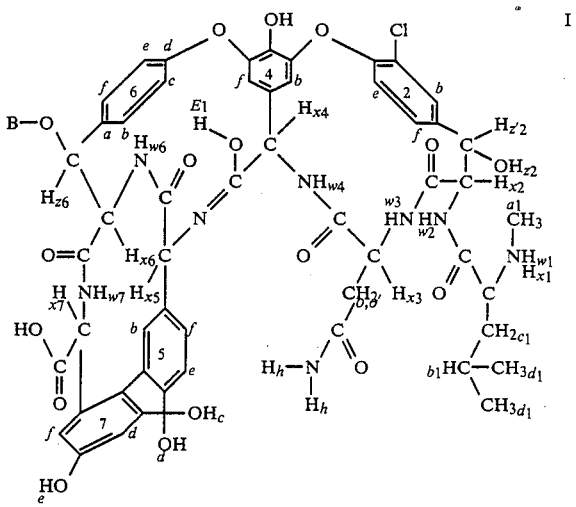

wherein B is as defined above.

In view of their similarities, in the present description and claims, when dealing with the biological properties of the compound of the invention, also its internal salt as well as its basic and acid addition salts are intended.

Antibiotic A 42867 pseudoaglycon is prepared from antibiotic A 42867 by controlled acid hydrolysis, conducted in an organic solvent in the presence of a strong acid.

The reaction temperature is preferably between 40° C. and 110° C. and most preferably between 80° C. and 100° C., with about 90° C. being the most preferred reaction temperature.

The reaction time varies depending on the specific reaction conditions.

Generally, the reaction time is between 1 h and 120 h. However, since the reaction course may be monitored by TLC or HPLC, the skilled man is capable of deciding when the hydrolysis of the starting materials is to be considered as completed and the recovery procedure may be started.

Representative examples of strong acids are mineral or organic strong acids such as hydrogen halides, e.g. hydrogen chloride, bromide and iodide, phosphoric acid, sulfuric acid, haloacetic acids, e.g. trichloroacetic acid, trifluoroacetic acid, chlorodifluoroacetic acid and the like.

Suitable organic solvents are such that:

(a) they may at least partially solubilize the starting materials;

(b) the products, once obtained, either separate or may be separated from them according to usual techniques, and (c) in any case, they do not unfavorably interfere with the reaction course.

Examples of said organic solvents are protic or aprotic solvents such as ($C_1$-$C_4$)alkyl sulfoxides, e.g. dimethylsulfoxide and diethylsulfoxide, ($C_1$-$C_4$)alkyl formamides, e.g. dimethylformamide, diethylformamide, dioxane, tetrahydrofuran and similar solvents, which are of course compatible with the selected acid.

In general, the hydrolysis is conducted in the presence of a limited amount of water, e.g. from 0.1 to 10% (w/w) of the reaction mixture. This amount of water can obviously be already present either in the starting materials, solvents and/or reagents, or may be added ad hoc, if necessary.

A preferred embodiment of the process of the invention, is represented by the use of a mixture dimethylsulfoxide/diluted hydrochloric acid at a temperature between 80° C. and 100° C. Typically, the ratio of the mixture dimethylsulfoxide/diluted hydrochloric acid is from 8:2 to 9.5:0.5. The preferred acid concentration is 0.1 N hydrochloric acid.

Antibiotic A 42867 pseudoaglycon obtained according to the above procedure may be further purified, if necessary or required, according to known per se techniques and preferably by chromatography such as liquid/liquid chromatography, flash chromatography, high pressure liquid chromatography and affinity chromatography.

When affinity chromatography is used, a preferred adsorbent is an immobilized D-Alanyl-D-Alanine as described in EP-A- 122969. Particularly preferred is agarose-epsilon-aminocaproyl-D-Alanyl-D-Alanine.

The elution mixture is a mixture of an aqueous buffer and a saline solution or an aqueous base.

A preferred eluent is a solution of a volatile base such as aqueous ammonia and most preferably is about 1.5% aqueous ammonia, while a preferred rinsing solution is phosphate buffer pH 6.0.

Alternatively, antibiotic A 42867 pseudoaglycon may be further purified by means of strong or weak anion resins including functionalized polystyrene, acrylic or polydextrane matrices. Examples of weak anion exchange resins are those sold under the following tradenames: Dowex MWA-1 or WGR (Dow Chemical), Amberlite IRA-73 (Rohm and Haas), DEAE-Sephadex (Pharmacia). Examples of strong anion exchange resins which may be used according to invention include those sold under the following trade names: Dowex MSA-1, SBR, SBR-P (Dow Chemical), Amberlite IR-904 (Rohm and Haas) and QAE-Sephadex (Pharmacia).

The elution of the antibiotic substance from these resins is conducted by means of linear gradient mixtures of aqueous solution of electrolytes, such as sodium or potassium hydrochlorides, in water or mixtures of water and an organic water-miscible solvent such as a lower alcohol (e. g. ($C_1$–$C_4$)alkanol) or lower alkyl ketones (e.g. acetone, methylethyl ketone, etc.)

If further purification is desired or necessary, it can be conveniently achieved by preparative HPLC.

A reverse phase silica gel is in this case used as the adsorbent while the mobile phase is one of those conventionally used in this field, such as a mixture of an aqueous buffer and a polar organic solvent. A preferred aqueous buffer is a sodium phosphate buffer, while a preferred polar organic solvent which can be conveniently used is acetonitrile.

Antibiotic A 42867 pseudoaglycon possesses acid and basic functions and besides forming internal salts, under proper pH conditions, can form salts with organic and inorganic counter-ions according to conventional procedures.

Representative and suitable acid addition salts of the compounds of the invention include those salts formed by standard reaction with both organic and inorganic acids such as, for example, hydrochloric, hydrobromic, sulfuric, phosphoric, acetic trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like acids.

Representative examples of these bases are: alkali metal or alkaline-earth metal hydroxide such sodium, potassium, calcium, magnesium, barium hydroxide; ammonia and aliphatic, alicyclic or aromatic organic amines such as methylamine, dimethylamine, trimethylamine, and picoline.

The transformation of the "non-salt" compounds of the invention into the corresponding addition salts, and the reverse, i.e. the transformation of an addition salt of a compound of the invention into the non-salt form, are within the ordinary technical skill and are encompassed by the present invention.

For instance antibiotic A 42867 pseudoaglycon can be transformed into the corresponding acid addition-salt by dissolving the non-salt form in an aqueous solvent and adding a slight molar excess of the selected acid or base. The resulting solution or suspension is then lyophilized to recover the desired salt.

In case the final salt is unsoluble in a solvent where the non-salt form is soluble it is recovered by filtration from the organic solution of the non-salt form after addition of the stoichometric amount or a slight molar excess of the selected acid or base.

The non-salt form can be prepared from a corresponding acid or base salt dissolved in an aqueous solvent which is then neutralized to free the non-salt form.

When following the neutralization the elimination of the excess of acid or base is necessary, a common desalting procedure may be employed.

For example, column chromatography on silanized silica gel, non-functionalized polystyrene, acrylic and controlled pore polydextrane resins (such as Sephadex LH 20) or activated carbon may be conveniently used. After eluting the undesired salts with an aqueous solution, the desired product is eluted by means of a linear gradient or a step-gradient of a mixture of water and a polar or apolar organic solvent, such as acetonitrile/water from 50:50 to about 100% acetonitrile.

As it is known in the art, the salt formation either with pharmaceutically acceptable acids (or bases) or non-pharmaceutically acceptable acids (or bases) may be used as a convenient purification technique. After formation and isolation, the salt form of antibiotic A 42867 pseudoaglycon can be transformed into the corresponding non-salt form or into a pharmaceutically acceptable salt form.

The antibacterial activity of the compound of the invention can be demonstrated in vitro by means of standard dilution tests on different microorganism cultures.

Culture media and growth conditions for MIC (minimal inhibitory concentration) determinations were as follows: Isosensitest broth (Oxoid), 24 h, for staphylococci, Strep. faecalis and Gram-negative bacteria (Escherichia coli); Todd-Hewitt broth (Difco), 24 h for other streptococcal species; GC base broth (Difco) +1% Isovitalex (BBL), 48 h, $CO_2$-enriched atmosphere for Neisseria gonorrhoeae; Brain Heart broth (Difco) +1% Supplement C (Difco), 48 h for Haemophilus influenzae. PPLO broth with supplements as in R. T. Evans and D. Taylor-Robinson (J. Antimicrob. Chemother. 4, 57), 24 h for U. urealyticum. Incubation was at 37° C. Inocula were as follows: about $10^4$ color-changing units/ml for U. urealyticum; about $10^4$–$10^5$ colony-forming units/ml for other broth dilution MICs.

The minimal inhibitory concentrations (MIC, microgram/ml) for some microorganisms are reported below in Table I.

TABLE I

| Strain | M.I.C. (microgram/ml) Antibiotic A 42867 pseudoaglycon |
|---|---|
| Staph. aureus L 165 ($10^4$ cfu/ml) | 1 |
| Staph. aureus $10^6$ cfu/ml | 1 |
| Staph. aureus 30% bovine serum | 2 |
| Staph. epidermidis L 147 ATCC 12228 (coagulase negative) | 2 |
| Staph. haemolyticus clin isolate | 2 |
| Strep. pyogenes L 49 C 203 | 0.5 |
| Strep. pneumoniae L 44 UC 41 | 1 |
| Strep. faecalis L 149 ATCC 7080 | 2 |
| Strep. mitis L 796 (clinical isolate) | 0.5 |
| Neisseria gonorrhoeae L 997 ISM 68/126 | 64 |
| Haemophilus influenzae type b L 970 ATCC 19418 | >128 |
| Ureaplasma urealyticum 1479 clin. isolate | >128 |
| Escherichia coli L 47 SKF 12140 | >128 |

The antimicrobial activity of the compounds of the invention is confirmed also in experimental septicemia in the mouse.

Control and treatment groups contain ten CD-1 mice (Charles River) weighing 18-22 g. They are infected intraperitoneally with 0.5 ml of bacterial suspension prepared by diluting an overnight culture of *S. pyogenes* C 203 (L 49) with sterile peptonized saline. Inocula are adjusted so that untreated animals died of septicemia within 48 h. The compounds to be tested are administered subcutaneously immediately after infection. On the 7th day, the $ED_{50}$ in mg/kg is calculated by the method of Spearman and Kärber (D. J. Finney "Statistical Methods in Biological Assay", Griffin, page 524, 1952) from the percentage of surviving animals at each dose.

In general, for antibacterial treatment antibiotic A 42867 pseudoaglycon as well as the non-toxic pharmaceutically acceptable salts thereof or mixture thereof, can be administered by different routes such as topically or parenterally. The parenteral administration is, in general, the preferred route of administration.

Compositions for injection may take such forms as suspensions, solutions, or emulsions in oily or aqueous vehicles, and may contain adjuvants such as suspending, stabilizing and/or dispersing agents.

Alternatively, the active ingredient may be in powder form for reconstitution at the time of delivery when a suitable vehicle, such as sterile water, is added thereto.

Depending on the route of administration, these compounds can be formulated into various dosage forms. In some instances, it may be possible to formulate the compounds of the invention in enteric-coated dosage forms for oral administration which may be prepared as known in the art (see for instance "Remington's Pharmaceutical Sciences", fifteenth edition, Mack Publishing Company, Easton, Penna. U.S.A., page 1614).

This could be especially the case when the absorption of the antimicrobial substance in the enteric tract is particularly desired while passing unaltered through the gastric tract.

The amount of active principle to be administered depends on various factors such as the size and condition of the subject to be treated, the route and frequency of administration, and the causative agent involved.

The antibiotic substances of the present invention and the physiologically acceptable salts thereof, are generally effective at a daily dosage of between about 0.5 and 50 mg of active ingredient per kilogram of patient body weight, optionally divided into 1 to 4 administrations per day.

Particularly desirable compositions are those prepared in dosage units containing from about 100 to about 5,000 mg per unit.

Representative examples of vehicles suitable for injection are: sterile water for injection, Ringer's solution, 0.9% saline and 5% dextrose.

For i.v. infusion, the suitable concentration of the antibiotic in the vehicle is between about 5% and 10%.

Other suitable formulations for dosage units are hermetically sealed vials, plastic pouches, sterile, rubber-stoppered vials and the like.

In addition, the antibiotic substance of the invention can be formulated in a topical preparation such as a solution, a cream or a lotion. These preparations conveniently contains from 0.1 to 15% (w/v) of the active ingredient.

Besides its activity as medicament, antibiotic A 42867 pseudoaglycon, or an acceptable salt thereof, can be used as an animal growth promoter.

For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and CO., S. Francisco, U.S.A., 1969 or "Livestock Feeds and Feeding" O and B books, Corvallis, Ore., U.S.A., 1977) and are incorporated herein by reference.

Physico-chemical characteristics of antibiotic A 42867:

(A) ultraviolet absorption spectrum which exhibits the following absorption maxima:

|     |                         | Lambda max (nm) |
| --- | ----------------------- | --------------- |
| (a) | 0.1 N HCl               | 282             |
| (b) | Water                   | 282             |
| (c) | phosphate buffer pH 7.4 | 282             |
| (d) | phosphate buffer pH 9   | 282             |
|     |                         | 305 (shoulder)  |
| (e) | phosphate buffer 0.1 N KOH | 305          |
|     |                         | 265 (shoulder)  |

(B) infrared absorption spectrum which exhibits the following absorption maxima ($cm^{-1}$): 3700–3100, 3000–2800 (nujol); 1650; 1580; 1460 (nujol) 1375 (nujol); 1300; 1235; 1210; 1160; 1130; 1060; 1025; 1000; 970; 840; 790–700; 720 (nujol)

(C) $^1$H-NMR spectrum reported in FIG. 4 of the attached drawings which exhibits the following groups of signals (in ppm) at 500 MHz recorded in DMSO $d_6$ (hexadeuterodimethylsulfoxide) using TMS as the internal standard (0.00 ppm), (delta=ppm): $d_1$ 0.90; $R_6$ 1.06; $V_6$ 1.23; $V_3$ 1.52; $c_1$ 1.62; $b_1$ 1.76; $V_2$, $V_2'$ ~2.30; $a_1$(-N—$CH_3$)2.38; $R_4$3.12; $x_1,R_3,V_4$ 3.10–3.50; $V_5$ 3.60; $R_2$ 3.79; $x_6$, $R_5$ 4.22; $x_7$4.51; $x_5$ 4.75; $V_1$ 4.88; $R_1$ 4.96; $x_2$ 5.02; $x_3$, $z_6$ 5.12; $z'_2$ 5.22; 4f 5.33; 4b 5.53; $(z_2)$OH 5.88; 7f 6.23; $x_4$ 6.34; 7d 6.41; h 6.62; $5c,w_3$ 6.76; 5f 6.84; 6c 7.12; 5b 7.15; 2b 7.26; $w_6$,h 7.32; 6b 7.50; $w_4$ 8.15; $w_7$ 8.45; 7c 9.10; 5d,$e_1$ 9.32; 7e 9.39;

(D) retention-time ($R_t$) of 0.665 relative to Vancomycin.HCl(Vancocin,Eli Lilly, $r_t$ 9.96 min) when analyzed by reverse phase HPLC under the following conditions:

column: Ultrasphere ODS (5 micrometer) Altex (Beckman) 4.6 mm (i.d.)×250 mm
pre-column: Brownlee Labs RP 18 (5 micrometer)

| eluent A: $CH_3CN$ | 2% | adjusted at |
| --- | --- | --- |
| (2.5 g/l) $NaH_2PO_4.H_2O$ | 98% | pH 6.0 |
| eluent B: $CH_3CN$ | 70% | adjusted at |
| (2.5 g/l) $NaH_2PO_4.H_2O$ | 30% | pH 6.0 | elution: linear gradient from 5% to 60% of eluent B in eluent A, in 40 min flow rate: 1.6 ml/min U.V. detector: 254 nm internal standard: Vancomycin.HCl ($R_t=9.96$ min) (Vancocin, Eli Lilly)

(E) elemental analysis, after the sample has been previously dried at about 140° C. under inert atmosphere which indicates the following approximate percentage composition (average): carbon 53.3%; hydrogen 5.9%; nitrogen 7.85%; chlorine (total) 4.41%; chlorine (ionic) 2.22%. Inorganic residue at 900° C. in the air: 0.875%.

(F) acid-base titration profile in water upon titration with 0.05N aqueous KOH of a sample previously added with excess of aqueous HCl which shows pKa values at 3.2, 7.1 and 8.3

(G) $R_f$ value of 0.56 in the following chromatographic system:

a mixture of aqueous NaCl (87.5 g/l):aqueous $NaH_2PO_4$ (0.5 g/l), and acetonitrile, 70:30, adjusted to pH 6.0 using reverse-phase silanized silica gel plates (RA-18 $F_{254}$)

Visualization:

U.V. light at 254 nm

Yellow color with Pauly Reagent, i.e. diazotized sulfanilic acid (J. Chromatog. 20, 171 (1965), Z. Physiol. Chem. 292, 99, (1953))

Bioautography using B. subtilis ATCC 6633 on minimal Davis medium.

(H) MW of about 1559 desumed from a FAB-MS spectrum showing the M+H+ peak at 1560.

In particular, the symbol:

- - - - - - - refers to the assay in 0.1 HCl

───▲─── refers to the assay in water

───■─── refers to the assay in phosphate buffer pH 7.4

───●─── refers to the assay in 0.1 N KOH

Figure 1:
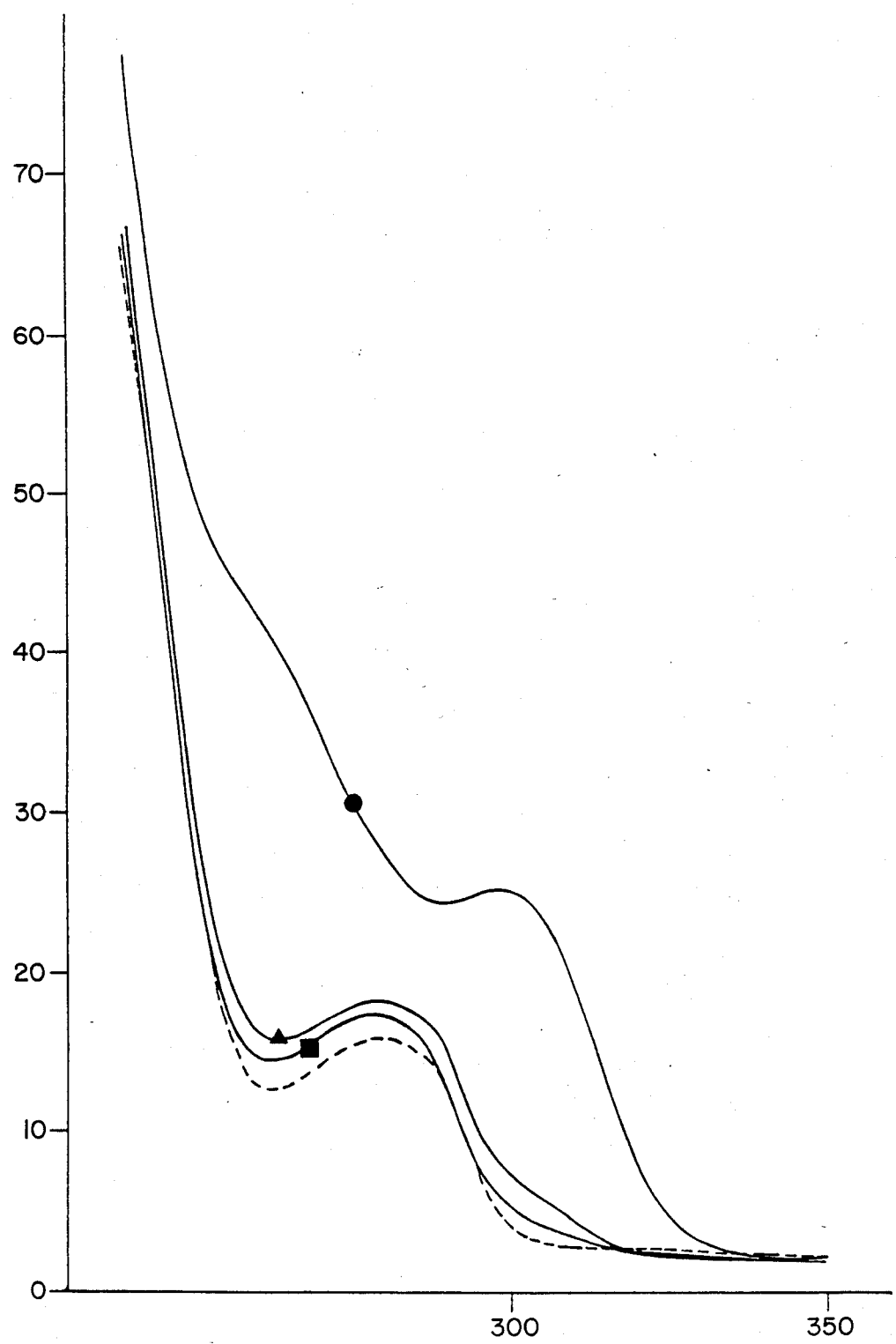
FIG. 1 relates to the U.V. spectrum of antibiotic A 42867 pseudoaglycon under the conditions reported above.
Figure 2:
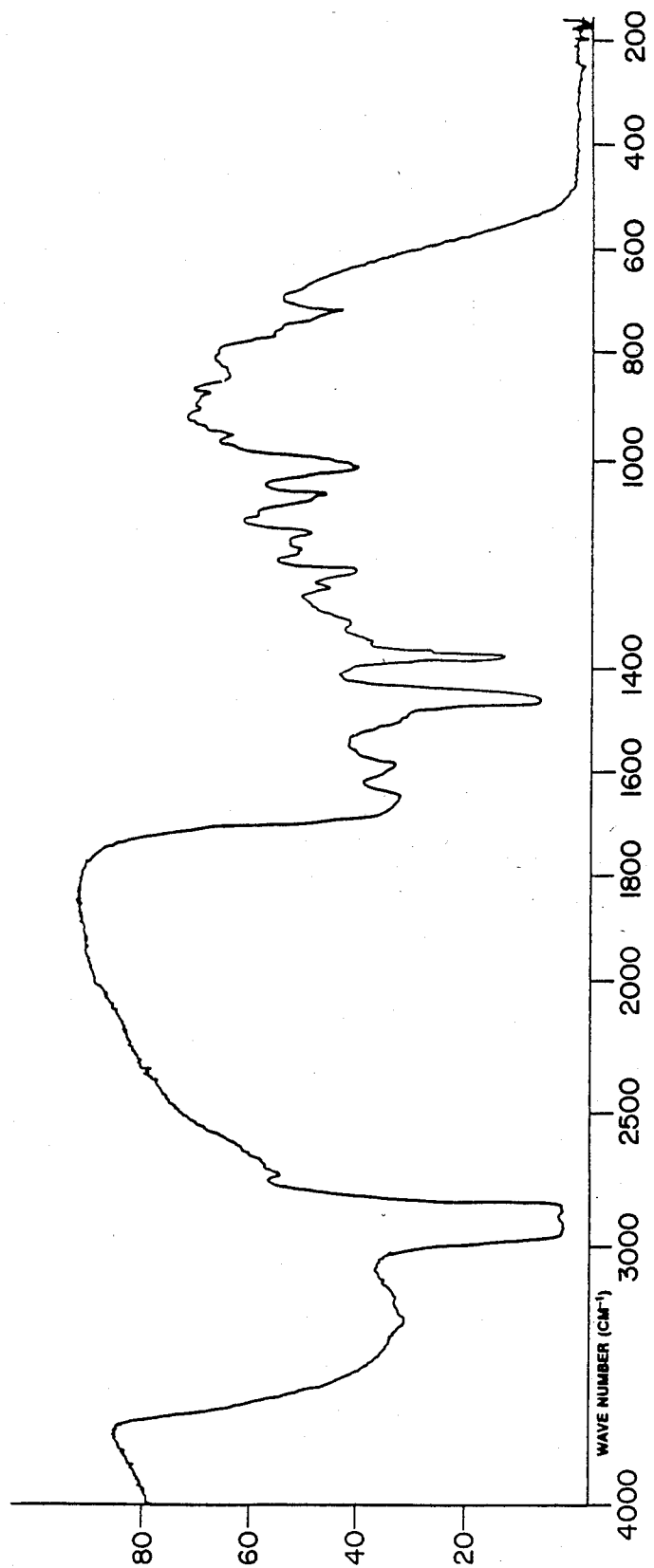

FIG. 2 relates to the I.R. absorption spectrum of antibiotic A 42867 pseudoaglycon under the conditions reported above.

Figure 3:
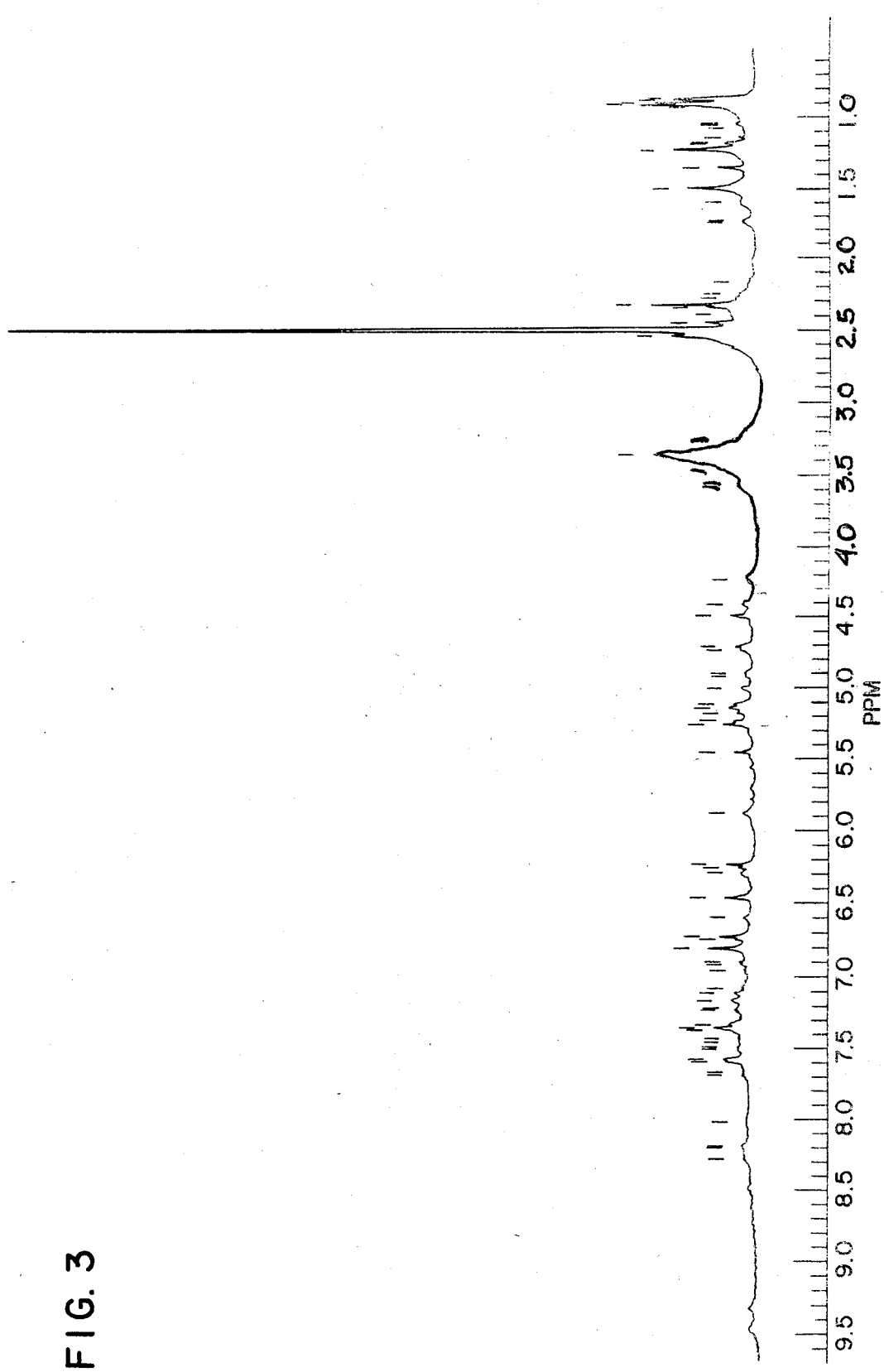

FIG. 3 relates to the $^1$H-NMR spectrum of antibiotic A 42867 pseudoaglycon under the conditions reported above.

Figure 4:
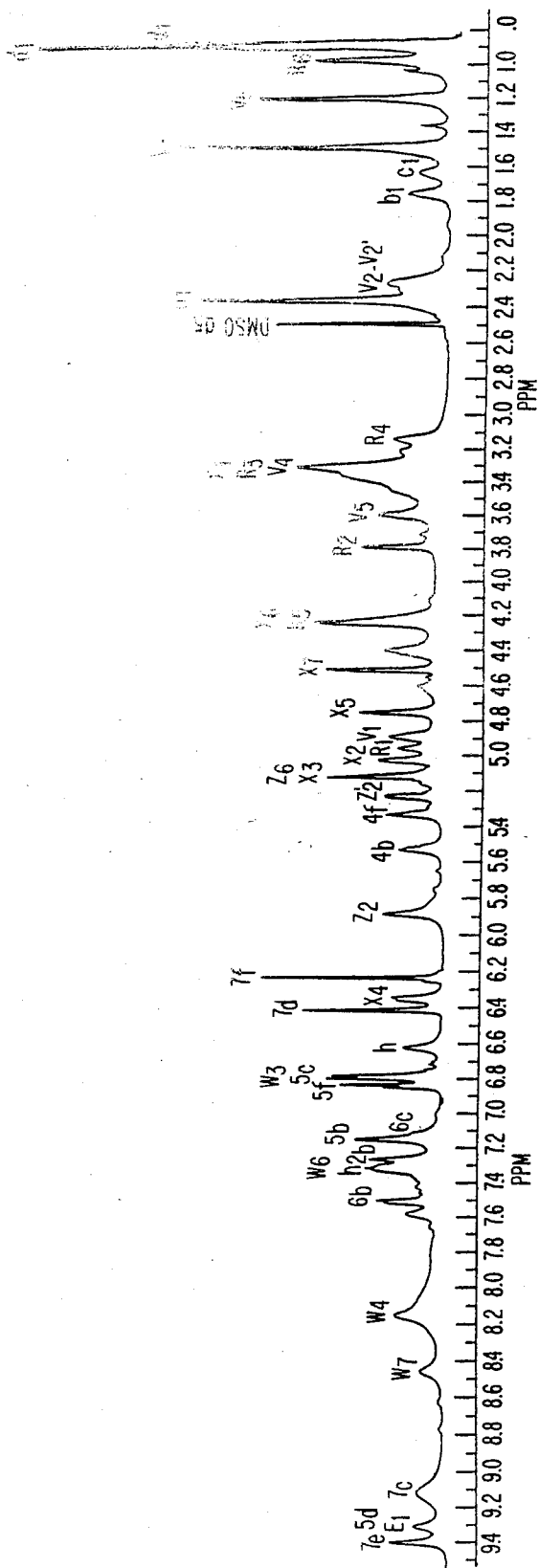

FIG. 4 relates to the $^1$H-NMR spectrum of antibiotic A 42867 under the conditions reported above. The letters over each signal represent the attribution given to it.

PREPARATION 1

Production of antibiotic A 42867

The stock culture of the producing organism (Nocardia sp. ATCC 53492) is streaked on oatmeal agar slants and incubated at 28° C. for 2 weeks.

One loopful of strain growth is inoculated into a 500 ml Erlenmayer flask containing 100 ml of a seed medium composed of dextrose 2.0%, soybean meal 0.8%, yeast extract 0.2%, NaCl 0.1% and $CaCO_3$ 0.4% whose pH of the medium has been adjusted to 7.3 before sterilization.

The flask is incubated on a rotary shaker at 28° C. for 72 hours. A 100 ml aliquot of the culture is then inoculated into a jar-fermentor containing 4 liters of the same seed medium and the culture is incubated at 28° C. for 48 hours with agitation of about 900 rpm and aeration of one standard liter of air per volume per minute.

After inoculation of 4 liters of the seed culture into a jar fermentor containing 200 liter of fermentation medium having the same composition as the seed medium, fermentation is carried out for 96 hours with agitation of about 250 rpm and aeration of one standard liter of air per volume per minute:

The antibiotic activity was monitored by microbiological assay using B. subtilis cultured on minimal Davis medium.

PREPARATION 2

Recovery of antibiotic A 42867

The whole fermentation broth (400 liters) obtained as described in Preparation 1 is filtered using a filter aid (Hyflo-FloMa ®), on a rotatory filter. The filtered broth is adjusted to pH 7.5 with 2 N hydrochloric acid, and added to 1000 ml of pre-swollen D-Ala-D-Ala-amino-caproyl-Sepharose-4B modified matrix (prepared as described in EP-A- 122969) and left overnight under slight stirring.

The resin is recovered by filtration and washed with about 10 of 0.5% (w/v) HCl-Tris buffer pH 7.5 which contains 5% (w/v)NaCl and then with water (4×5 l) while the broth is discharged.

The product selectively bound to the resin is eluted with 1.5% (w/v) ammonia hydroxide (4×5 l) and concentrated to a small volume (about 1800 ml) by means of azeotropical distillation with n-butanol under reduced pressure.

The concentrated aqueous solution is lyophilized obtaining crude antibiotic A 42867 (75.6 g).

PREPARATION 3

Purification of crude antibiotic A 42867

Crude antibiotic A 42867 obtained by following the procedure of Preparation 2 (75 g) is dissolved in 2 liters of water containing 2 M sodium chloride, adjusted to pH 7.5 with 0.1 N sodium hydroxide solution, and then filtered.

The filtrate is applied at 500 ml/hour to a 1000 ml column (0.1×0.1 m) of pre-swollen D-Ala-D-Ala-6-amino- caproyl-Sepharose-4B modified matrix (prepared as described in EP-A- 122969) previously equilibrated with 0.04 M borate buffer pH 7.5 containing 2 M sodium chloride and 0.6 ml of Triton×100 (Baker grade).

The column is washed with 8 l of 8 M urea (pH 7.5) with flow rate of 500 ml/h followed by 70 l of aqueous NaOH at pH 10 collecting fractions of 1000 ml each.

These fractions are assayed on B. subtilis cultures by agar-disc assay and those fractions which are inactive are discharged while those active (like fractions 63–70, in this case) are combined, concentrated to a small volume (500 ml) under reduced pressure by means of azeotropical distillation with n-butanol and lyophilized to give antibiotic A 42867 (4 g).

PREPARATION 4

Purification and desalination of antibiotic A 42867

3.5 g of antibiotic A 42867 obtained by following the procedure of Preparation 3 is dissolved in 70 ml of a solution of sodium dihydrogen phosphate monohydrate (2.5 g/l) and acetonitrile (91:9) and filtered.

10 ml of this filtrate is applied to a stainless steel column (2×50 cm) packed with 40 g of 10 micrometer RP 18 Lichrosorb reverse-phase silica gel (Merck).

The column is part of a Chromatospac Modulprep unit (Jobin Yvon, 16-18 Rue de Canal 91169 Longjumeau, France).

The column is eluted at 8 ml/min with the same solution used to dissolved the sample and fractions of 50 ml are collected.

Each fraction is monitored by HPLC and paper-disc bioassay on suceptible microorganisms such as *B. subtilis*.

The fractions active on *B. subtilis* of seven runs are combined, acetonitrile is removed by distillation under reduced pressure and the residue is diluted with a quantity of water which was about the volume of the initial solution.

The solution is adjusted to pH 7.5 and later applied a flow rate of 100 ml/h to a column (5×15 cm) of pre-swollen D-Ala-D-Ala-6-aminocaproyl-Sepharose-4B modified matrix (prepared as described in EP-A-122969) previously equilibrated with 0.04 M borate buffer pH 7.5.

The column is washed with 8 l of water (acidifed with 0.5 ml/l of 1 N hydrochloric acid).

The column is then eluted with 1.5% (w/v) ammonia hydroxide collecting fractions of 100 ml each.

Those fractions active against *B. subtilis* are pooled, concentrated under pressure and lyophilized to give 1.2 g of a desalted preparation of antibiotic A 42867 whose physico-chemical characteristics are reported before.

The following examples further illustrate the invention but should not be interpreted as limiting it in any way.

EXAMPLE 1

Preparation of antibiotic A 42867 pseudoaglycon

Antibiotic A 42867 prepared substantially according to Preparation 3 (1 g) is dissolved in a mixture dimethyl-sulfoxide/1N hydrochloric acid, 9:1 (35 ml) and heated to 85° C.-90° C.

The reaction course is monitored by HPLC and when the starting materials are about completely reacted (after about 15 h) the reaction is quenched with 0.1 M sodium phosphate buffer pH 7.0 (250 ml). Antibiotic A 42867 pseudoaglycon is separated from this mixture by the following affinity procedure:

The aqueous mixture obtained above (750 ml) is applied to a Sepharose-D-Alanyl-D-Alanine chromatography column prepared as described in EP-A- 122969 (200 ml of swollen resin in 10 mM TRIS.HCL pH 7.5 buffer; bed height 10 cm).

This column is rinsed with 0.1 M sodium phosphate buffer pH 7.0, monitoring the eluates with U.V. light (254 nm) until no absorbance is detected. Then the column is eluted with 1.5% (w/v) ammonia (about 1, flow rate 200 ml/h) and the eluate concentrated to a small volume under reduced pressure by azeotropical distillation with n-butanol and lyophilized yielding antibiotic A 42867 pseudoaglycon (349 mg; HPLC purity: 85%).

By repeating this experiment but using a mixture DMSO/1 M HCl 8.5:1.5 at 100° C. for about 10 h or a mixture DMSO/1 M HCl 9.5:0.5 at 90° C. for about 12 h, the compound of the title is obtained.

EXAMPLE 2

Further purification of antibiotic A 42867 pseudoaglycon

Antibiotic A 42867 pseudoaglycon obtained (250 mg) is dissolved in a mixture of sodium dihydrogen phosphate monohydrate (2.5 g/l) and acetonitrile, 92:8, adjusted to pH 6 (5 ml).

This solution (1 ml) is applied to a HPLC semi-preparative pre-packed column (250×10 mm (i.d.), Merck, packed with reverse phase silica gel Lichrosorb RP 18, 7 micrometer) which is then eluted with a flow rate of 4 ml/min of a mixture of phase A and phase B with a linear gradient from 5% to 50% of phase B in A.

Phase (A) (2.5 gr/l) $NaH_2PO_4/CH_3CN$ 98:2 (v/v) adjusted to pH 6.0 with NaOH.

Phase (B) (2.5 gr/l) $NaH_2PO_4/CH_3CN$ 30:70 (v/v) adjusted to pH 6.0 with NaOH.

The eluates are U.V. monitored at 254 nm and the eluted fractions with homogeneous content are pooled.

The eluates containing the purified antibiotic A 42867 pseudoaglycon of 5 subsequent chromatographic runs are pooled and desalted as usual by loading them on a column of 50 ml swollen sepharose-D-Ala-D-Ala. After removing the salts with 100 ml of 1 mM HCl, the antibiotic is eluted with 3×100 ml of 1.5% w/v aqueous ammonia. The ammonia eluates are then collected and concentrated under reduced pressure yielding 160 mg of pure antibiotic A 42867 pseudoaglycon.

We claim:

1. Antibiotic A 42867 pseudoaglycon and the pharmaceutically acceptable salts thereof having the following the formula (unsalified compound):

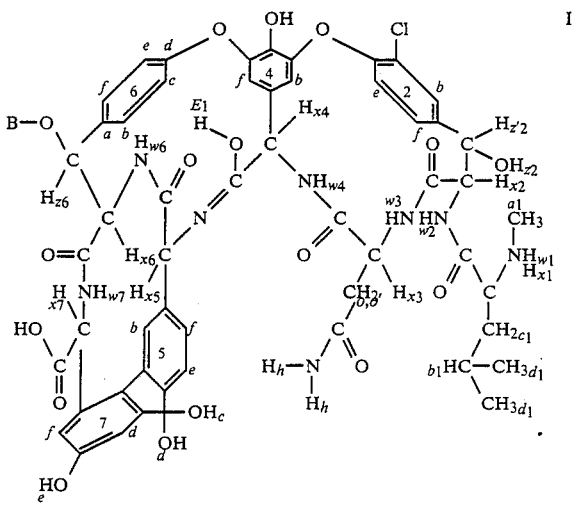

wherein
B represents a beta-vancosamine unit of formula

VANCOSAMINE (β anomer)

and the tautomers thereof.

2. Antibiotic A 42867 pseudoaglycon and the pharmaceutically acceptable salts thereof having the following physico-chemical parameters (unsalified form):
   (A) ultraviolet absorption which exhibits the following absorption maxima:

|     |                    | Lambda max (nm) |
| --- | ------------------ | --------------- |
| (a) | 0.1 N HCl          | 279             |
| (b) | Water              | 279             |
|     |                    | 305 (shoulder)  |
| (c) | phosphate buffer pH 7.4 | 279        |
| (e) | 0.1 N KOH          | 279             |
|     |                    | 299             |
|     |                    | 265 (shoulder)  |

(B) infrared absorption spectrum in nujol mull which exhibits the following absorption maxima (cm-$^{-1}$): 3700–3100, 3000–2800 (nujol); 1650; 1590; (nujol); 1375 (nujol); 1305; 1240; 1210; 1160; 1130; 1060; 1010; 950; 870; 835; 720 (nujol)

(C) $^1$H-NMR spectrum which exhibits the following groups of signals (in ppm) at 250 MHz (Bruker Instruments) recorded in DMSO d$_6$ (hexadeuterodimethylsulfoxide) using TMS as the internal standard (0.00 ppm), (delta=ppm):

Sugar moiety:
1.22,d [CH$_3$—(CH)]; 1.50,s [CH$_3$—C(NH$_2$)]; 2.25, m [CH$_2$—(CH)]; 3.60, m [CH—(CH$_3$)]; 4.90, d (anomeric proton)

Core moiety:

0.90, d and 0.94 [CH$_3$\\(CH)/CH$_3$];

1.74, m [CH(CH$_3$)$_2$];

1.60, m [CH$_2$(CH\\/CH)];

2.32, s [CH$_3$—(NH]; 2.49, s (solvent DMSOd$_5$); 3.35, br [H$_2$O]; 4.23–6.35 [aromatic and peptidic CH's]; 6.35–9.50 [aromatic CH's, peptidic NH's and phenolic OH's]

s=singlet; d=doublet; m=multiplet; br=broad (D) retention time (R$_t$) of 2.88 relative to antibiotic A 42867 (R$_t$=8.45 min) when analyzed by reverse phase HPLC under the following conditions:

column: Ultrasphere ODS (5 micrometer) Altex (Beckman) 4.6 mm (i.d.)×250 mm pre-column: 3 cm Brownlee Labs RP 18 (5 micrometer)

eluents:
(A) (2.5 gr/l) NaH$_2$PO$_4$/CH$_3$CN, 98:2 (v/v) adjusted to pH 6.0
(B) (2.5 gr/l) NaH$_2$PO$_4$/CH$_3$CN, 30:70 (v/v) adjusted to pH 6.0

Elution mode: linear gradient from 5% to 60% of B in A in 40 min flow rate: 1.8 ml/min U.V. detector: 254 nm internal standard: antibiotic A 42867 (R$_t$=8.45 min)

(E) elemental analysis showing the presence of one chlorine atom per molecule (F) 2D $^1$H-NMR NOESYPH analysis showing that the molecular chlorine atom is on ring 2 and not on ring 6, on the basis of Nuclear Overhauser effect (dipolar coupling through space) and scalar coupling through chemical bond, in fact:

(a) on the basis of scalar coupling, proton 2b (see formula I) shows only a meta coupling with 2f but no ortho coupling; (proton 2b is on ring 2 and not on ring 6 on the basis of the following dipolar coupling: 2b →Z'2; 2b →(Z2)OH; (Z2)OH →Z'2; Z'2→X2)

(b) on the basis of scalar coupling, proton 6b (see formula I) shows an ortho coupling with proton 6c (dipolar coupling 6b→6c; Z6-6b; Z6→X6)

(G) a fast atom bombardment (FAB) mass spectrum with M+H$^+$ at about 1251 (the theoretical cluster ion peaks for the formula C$_{60}$H$_{64}$N$_9$O$_{19}$Cl+H range from 1250 to 1255, average value 1251.68). The FAB spectrum was obtained with a VG 70-250 instrument, bombarding gas Xenon; beam energy 8 KV; accelerating voltage 6kV; matrix thioglycerol-glycerol, 2:.

(H) acid and basic functions capable of forming salts.

3. A process for preparing a compound of claim 1 which comprises reacting a compound of formula II

II wherein

A represents a disaccharide residue of one unit of glucose and one unit of d-rhamnose, of formula, respectively:

GLUCOSE

RHAMNOSE
(α anomer)

and
B represents a beta-vancosamine unit of formula

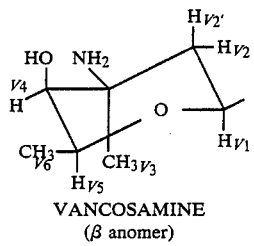

VANCOSAMINE
(β anomer)

or a tautomer thereof, under controlled acid hydrolysis at a temperature range of from 40° C. to 100° C. in an organic solvent and in the presence of an effective amount of a suitable strong acid.

4. A process for preparing a compound of claim 2 which comprises reacting Antibiodic A 42867 having the following characteristics:

(A) ultraviolet absorption spectrum which exhibits the following absorption maxima:

|   |   | Lambda max (nm) |
|---|---|---|
| (a) | 0.1 N HCl | 282 |
| (b) | Water | 279 |
| (c) | phosphate buffer pH 7.4 | 282 |
| (d) | phosphate buffer pH 9 | 282 |
|   |   | 305 (shoulder) |
| (e) | ogisogate byffer 0.1 N KOH | 305 |
|   |   | 265 (shoulder) |

(B) infrared absorption spectrum which exhibits the following absorption maxima (cm$^{-1}$): 3700–3100, 3000–2800 (nujol); 1650; 1580; 1460 (nujol) 1375 (nujol); 1300; 1235; 1210; 1160; 1130; 1060; 1025; 1000; 970; 840; 790–700; 720 (nujol)

(C) $^1$H-NMR spectrum which exhibits the following groups of signals (in ppm) at 500 MHz recorded in DMSO $d_6$ (hexadeuterodimethylsulfoxide) using TMS as the internal standard (0.00 ppm), (delta=ppm): $d_1$ 0.90; $R_6$ 1.06; $V_6$ 1.23; $V_3$1.52; $c_1$1.62; $b_1$1.76; $V_2,V_2'$~2.30; $a_1$ (N—CH$_3$) 2.38; $R_4$3.12; $x_1,R_3$, $V_4$3.10–3.50; $V_5$3.60; $R_2$ 3.79; $x_6$, $R_5$ 4.22; $x_7$ 4.51; $x_5$4.75; $V_1$ 4.88$R_1$4.96; $x_2$ 5.02; $x_3,z_6$ 5.12; $z'_2$ 5.22; 4f 5.33; 4b 5.53; ($z_2$)OH 5.88; 7f 6.23; $x_4$ 6.34; 7d 6.41; h 6.62; 5c,$w_3$6.76; 5f 6.84; 6c 7.12; 5b 7.15; 2b 7.26; $w_6$,h 7.32; 6b 7.50; $w_4$ 8.15; $w_7$ 8.45; 7c 9.10; 5d,$e_1$9.32; 7e 9.39;

(D) retention-time ($R_t$) of 0.665 relative to Vancomycin.HCl (Vancocin, Eli Lilly, $R_t$9.96 min) when analyzed by reverse phase PHLS under the following conditions:

column: Ultrasphere ODS (5 micrometer) Altex (Beckman) 4.6 mm (i.d.)×250 mm
pre-column: Brownlee Labs RP 18 (5 micrometer)

| eluent A: | CH$_3$CH | 2% | } | adjusted at pH 6.0 |
|---|---|---|---|---|
|   | (2.5 g/l) NaH$_2$PO$_4$.H$_2$O | 98% | | |

| eluent B: | CH$_3$CN | 70% | } | adjusted at pH 6.0 |
|---|---|---|---|---|
|   | (2.5 g/l) NaH$_2$PO$_4$.H$_2$O | 30% | | | elution: linear gradient from 5% to 60% of eluent B in eluent A, in 40 min
flow rate: 1.6 ml/min
U.V. detector: 254 nm
internal standard: Vancomycin.HCl ($R_t$=9.96 min) (Vanococin, Eli Lilly)

(E) elemental analysis, after the sample has been previously dried at about 140° C. under inert atmosphere which indicates the following approximate percentage composition (average): carbon 53.3%; hydrogen 5.9%; nitrogen 7.85%; chlorine (total) 4.41%; chlorine (ionic) 2.22%. Inorganic residue at 900° C. in the air: 0.875%.

(F) acid-base titration profile in water upon titration with 0.05N aqueous KOH of a sample previously added with excess of aqueous HCl which shows pKa values at 3.2, 7.1 and 8.3

(G) $R_f$ value of 0.56 in the following chromatographic system:
a mixture of aqueous NaCl (87.5 g/l):aqueous NaH$_2$PO$_4$ (0.5 g/l), and acetonitrile, 70:30, adjusted to pH 6.0
using reverse-phase silanized silica gel plates (RA-18 F254) Visualization:
U.V. light at 254 nm
Yellow color with Pauly Reagent, i.e. diazotized sulfanilic acid (J. Chromatog. 20, 171 (1965), Z. Physiol. Chem. 292, 99, (953))
Bioautography using *B. subtillis* ATCC 6633 on minimal Davis medium, (H) MW of about 1559 desumed from a FAB-MS spectrum showing the M+H$^+$ peak at 1650, under controlled acid hydrolysis at a temperature range of 40° C. to 110° C. in an organic solvent and in the presence of an effective amount of a suitable strong acid.

5. A process according to claim 3 wherein the strong acid is hydrochloric acid.

6. A process according to claim 5 wherein the solvent is dimethylsulfoxide or dimethylformamide.

7. A process according to claim 6 wherein the reaction temperature is between 80° C. and 110° C.

8. A pharmaceutical composition comprising a compound of claim 1 present in an effective amount in admixture with a pharmaceutically acceptable vehicle.

9. A method for the treatment of bacterial infections comprising administering to a patient in need thereof an effective amount of a compound according to claim 1.

10. A method for the treatment of bacterial infections comprising administering to a patient in need thereof an effective amount of a compound according to claim 2.

11. A pharmaceutical composition comprising a compound of claim 2 present in an effective amount in admixture with a pharmaceutically acceptable vehicle.

* * * * *